(12) United States Patent
Umberger et al.

(10) Patent No.: US 12,220,256 B2
(45) Date of Patent: Feb. 11, 2025

(54) AUTONOMOUS EVENT ASSISTANT DEVICE

(71) Applicant: WEST AFFUM HOLDINGS DAC, Dublin (IE)

(72) Inventors: Traci S. Umberger, Kirkland, WA (US); Krystyna Szul, Seattle, WA (US)

(73) Assignee: West Affum Holdings DAC, Dublin (IE)

( * ) Notice: Subject to any disclaimer, the term of this patent is extended or adjusted under 35 U.S.C. 154(b) by 238 days.

(21) Appl. No.: 17/390,845

(22) Filed: Jul. 30, 2021

(65) Prior Publication Data
US 2022/0054083 A1    Feb. 24, 2022

Related U.S. Application Data

(60) Provisional application No. 63/069,638, filed on Aug. 24, 2020.

(51) Int. Cl.
    *A61B 5/00*        (2006.01)
    *A61B 5/024*     (2006.01)
    (Continued)

(52) U.S. Cl.
    CPC ............ *A61B 5/68* (2013.01); *A61B 5/02438* (2013.01); *A61B 5/7282* (2013.01); *A61N 1/39* (2013.01);
    (Continued)

(58) Field of Classification Search
    CPC .... G08B 25/016; G08B 21/0453; A61N 1/39; A61B 5/68; A61B 5/02438; A61B 5/7282
    (Continued)

(56) References Cited

U.S. PATENT DOCUMENTS

| | | | |
|---|---|---|---|
| 3,724,355 | A | 4/1973 | Busch et al. |
| 3,724,455 | A | 4/1973 | Unger |

(Continued)

FOREIGN PATENT DOCUMENTS

| | | | | |
|---|---|---|---|---|
| CA | 2659939 A1 | * | 2/2007 | ............... A61N 1/39 |
| CN | 107730850 A | * | 2/2018 | ........... G08B 25/009 |

(Continued)

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

(Continued)

*Primary Examiner* — Michael J Lau
(74) *Attorney, Agent, or Firm* — Polsinelli PC

(57) ABSTRACT

A person living with an increased risk of a potentially life threatening condition that could at any moment render the person incapacitated, may find it stressful to be left alone for any length of time even if wearing a monitoring and/or treatment device. Wearers of monitoring and/or treatment systems may find it reassuring that should they become incapacitated when the monitored event occurs, the monitoring system can obtain information during the "blind" time, that is the time between the event onset and rescue arrival. An event assistant device, responsive to a wearable monitoring device's detection of an event, can navigate to the wearable monitoring device and capture visual and/or audio information for handoff to a designated rescuer.

20 Claims, 8 Drawing Sheets

(51) Int. Cl.
*A61N 1/39* (2006.01)
*G08B 21/04* (2006.01)
*G08B 25/01* (2006.01)

(52) U.S. Cl.
CPC ....... *G08B 21/0453* (2013.01); *G08B 25/016* (2013.01)

(58) Field of Classification Search
USPC ........................................................ 600/301
See application file for complete search history.

(56) References Cited

U.S. PATENT DOCUMENTS

| | | | |
|---|---|---|---|
| 4,583,524 A | 4/1986 | Hutchins | |
| 4,619,265 A | 10/1986 | Morgan et al. | |
| 4,666,432 A | 5/1987 | McNeish et al. | |
| 4,698,848 A | 10/1987 | Buckley | |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,348,008 A | 9/1994 | Bornn et al. | |
| 5,353,793 A | 10/1994 | Bornn | |
| RE34,800 E | 11/1994 | Hutchins | |
| 5,394,892 A | 3/1995 | Kenny | |
| 5,405,362 A | 4/1995 | Kramer et al. | |
| 5,429,593 A | 7/1995 | Matory | |
| 5,474,574 A | 12/1995 | Payne et al. | |
| 5,618,208 A | 4/1997 | Crouse et al. | |
| 5,662,690 A | 9/1997 | Cole et al. | |
| 5,708,978 A | 1/1998 | Johnsrud | |
| 5,741,306 A | 4/1998 | Glegyak et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,280,461 B1 | 8/2001 | Glegyak et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder | |
| 6,427,083 B1 | 7/2002 | Owen et al. | |
| 6,437,083 B1 | 7/2002 | Owen et al. | |
| 6,450,942 B1 | 9/2002 | Lapanashvili et al. | |
| 6,529,875 B1 | 3/2003 | Nakajima | |
| 6,546,285 B1 | 4/2003 | Owen et al. | |
| 6,671,545 B2 | 12/2003 | Fincke | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,099,715 B2 | 8/2006 | Korzinov et al. | |
| 7,212,850 B2 | 5/2007 | Prystowsky et al. | |
| 7,559,902 B2 | 7/2009 | Ting et al. | |
| 7,587,237 B2 | 9/2009 | Korzinov et al. | |
| 7,753,759 B2 | 7/2010 | Pintor et al. | |
| 7,865,238 B2 | 1/2011 | Brink | |
| 7,870,761 B2 | 1/2011 | Valentine et al. | |
| 7,907,996 B2 | 3/2011 | Prystowsky et al. | |
| 7,941,207 B2 | 5/2011 | Korzinov | |
| 7,974,689 B2 | 7/2011 | Volpe et al. | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,527,028 B2 | 9/2013 | Kurzweil et al. | |
| 8,548,557 B2 | 10/2013 | Garstka et al. | |
| 8,560,044 B2 | 10/2013 | Kurzweil et al. | |
| 8,615,295 B2 | 12/2013 | Savage et al. | |
| 8,644,925 B2 | 2/2014 | Volpe et al. | |
| 8,676,313 B2 | 3/2014 | Volpe et al. | |
| 8,706,255 B2 | 4/2014 | Phillips et al. | |
| 8,742,349 B2 | 6/2014 | Urbon et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,084,583 B2 | 7/2015 | Mazar et al. | |
| 9,089,685 B2 | 7/2015 | Sullivan et al. | |
| 9,119,547 B2 | 9/2015 | Cazares et al. | |
| 9,131,901 B2 | 9/2015 | Volpe et al. | |
| 9,132,267 B2 | 9/2015 | Kaib | |
| 9,265,432 B2 | 2/2016 | Warren et al. | |
| 9,345,898 B2 | 5/2016 | Piha et al. | |
| 9,408,548 B2 | 8/2016 | Volpe et al. | |
| 9,445,719 B2 | 9/2016 | Libbus et al. | |
| 9,454,219 B2 | 9/2016 | Volpe et al. | |
| 9,579,020 B2 | 2/2017 | Libbus et al. | |
| 9,592,403 B2 | 3/2017 | Sullivan | |
| 9,597,523 B2 * | 3/2017 | Kaib | A61N 1/3904 |
| 9,598,799 B2 | 3/2017 | Shoshani et al. | |
| 9,675,804 B2 | 6/2017 | Whiting et al. | |
| 9,724,008 B2 | 8/2017 | Sullivan et al. | |
| 9,878,171 B2 | 1/2018 | Kaib | |
| 9,895,105 B2 | 2/2018 | Romem | |
| 9,901,741 B2 | 2/2018 | Chapman et al. | |
| RE46,926 E | 7/2018 | Bly et al. | |
| 10,016,613 B2 | 7/2018 | Kavounas | |
| 10,076,656 B2 | 9/2018 | Dar et al. | |
| 10,092,767 B1 * | 10/2018 | Newton | A61N 1/3925 |
| 10,192,387 B2 | 1/2019 | Brinig et al. | |
| 10,307,133 B2 | 6/2019 | Kaib | |
| 10,332,423 B2 * | 6/2019 | Dellimore | A61B 5/0816 |
| 10,463,867 B2 | 11/2019 | Kaib et al. | |
| 10,589,110 B2 | 3/2020 | Oskin et al. | |
| 10,599,814 B2 | 3/2020 | Landrum et al. | |
| 11,158,179 B2 * | 10/2021 | Tunnell | G08B 27/001 |
| 11,253,716 B2 * | 2/2022 | Ogino | G16H 40/67 |
| 2002/0181680 A1 | 12/2002 | Linder et al. | |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2006/0173499 A1 | 8/2006 | Hampton et al. | |
| 2008/0312709 A1 | 12/2008 | Volpe et al. | |
| 2009/0005827 A1 | 1/2009 | Weintraub et al. | |
| 2010/0007413 A1 | 1/2010 | Herleikson | |
| 2010/0262367 A1 * | 10/2010 | Riggins | G08B 25/016 455/500 |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0191476 A1 | 7/2012 | Reid et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0144355 A1 | 6/2013 | Macho et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0012144 A1 | 1/2014 | Crone | |
| 2014/0025131 A1 | 1/2014 | Sullivan et al. | |
| 2014/0046391 A1 | 2/2014 | Cowan et al. | |
| 2014/0070957 A1 | 3/2014 | Longinotti-Buitoni et al. | |
| 2014/0163663 A1 | 6/2014 | Poddar et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0161554 A1 | 6/2015 | Sweeney et al. | |

(56) References Cited

U.S. PATENT DOCUMENTS

| | | |
|---|---|---|
| 2015/0265845 A1* | 9/2015 | Sullivan .............. A61N 1/3975 607/8 |
| 2015/0297135 A1 | 10/2015 | Shoshani et al. |
| 2015/0328472 A1 | 11/2015 | Sullivan et al. |
| 2016/0004831 A1 | 1/2016 | Carlson et al. |
| 2016/0076175 A1 | 3/2016 | Rock et al. |
| 2016/0076176 A1 | 3/2016 | Rock et al. |
| 2016/0082277 A1 | 3/2016 | Foshee, Jr. et al. |
| 2016/0113581 A1 | 4/2016 | Amir et al. |
| 2016/0256104 A1 | 9/2016 | Romem et al. |
| 2016/0283900 A1 | 9/2016 | Johnson et al. |
| 2016/0328529 A1* | 11/2016 | Kaib .................. G16H 40/40 |
| 2016/0328950 A1* | 11/2016 | Pelletier ............. G16H 40/67 |
| 2016/0331986 A1* | 11/2016 | Piha ................... G08B 21/0453 |
| 2016/0379476 A1* | 12/2016 | Sella ................. G08B 21/0453 340/539.19 |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0148241 A1* | 5/2017 | Kerning ............. H04W 12/08 |
| 2017/0162840 A1 | 6/2017 | Pendry |
| 2017/0319862 A1 | 11/2017 | Foshee, Jr. et al. |
| 2017/0367591 A1 | 12/2017 | Jorgensen |
| 2018/0039262 A1* | 2/2018 | Fox .................... H04W 4/02 |
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0241489 A1* | 8/2018 | Daoura ............... H04L 67/10 |
| 2018/0243578 A1 | 8/2018 | Volosin |
| 2018/0322749 A1* | 11/2018 | Kempel .............. G05D 1/0094 |
| 2018/0361165 A1 | 12/2018 | Jaax et al. |
| 2019/0030352 A1 | 1/2019 | Sullivan et al. |
| 2019/0065970 A1* | 2/2019 | Bonutti .............. G16H 20/10 |
| 2019/0076666 A1 | 3/2019 | Medema |
| 2019/0116896 A1 | 4/2019 | Armour et al. |
| 2019/0321650 A1 | 10/2019 | Raymond et al. |
| 2019/0329054 A1* | 10/2019 | Breske ............... A61N 1/3993 |
| 2019/0358464 A1* | 11/2019 | Volosin .............. A61B 5/024 |
| 2020/0038671 A1* | 2/2020 | Schulhauser ....... A61B 5/7275 |
| 2020/0206520 A1* | 7/2020 | Lui .................... A61N 1/3987 |
| 2020/0246217 A1 | 8/2020 | Freeman |
| 2020/0253483 A1* | 8/2020 | Chase ................ G06V 40/10 |
| 2022/0092957 A1* | 3/2022 | Beyer ................. H04W 4/023 |

FOREIGN PATENT DOCUMENTS

| | | | |
|---|---|---|---|
| DE | 102005060985 A1 | 6/2007 | |
| EP | 2305110 A1 | 4/2011 | |
| EP | 3380189 B1 | 10/2018 | |
| JP | 4320257 B2 | 8/2009 | |
| JP | 2014526282 A | 10/2014 | |
| JP | 5963767 B2 | 8/2016 | |
| WO | 1998039061 A2 | 9/1998 | |
| WO | 2011/146448 A1 | 11/2011 | |
| WO | 2012064604 A1 | 5/2012 | |
| WO | 2012/151160 A1 | 11/2012 | |
| WO | 2015/056262 A1 | 4/2015 | |
| WO | WO-2015132393 A1 * | 9/2015 | .......... G08B 21/043 |
| WO | WO-2017139922 A1 * | 8/2017 | ......... A61B 5/02108 |

OTHER PUBLICATIONS

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Metting Van Rijn, A. C., Peper A., & Grimbergen, C. A., High-Quality Recording of Bioelectric Events Part 1: Interference Reduction, Theory and Practice, Review, Medical & Biological Engineering & Computing, Sep. 1990, pp. 389-397, IFMBE.

Pagan-Carlo, et al., "Encircling Overlapping Multipulse Shock Waveforms for Transthoracic Defibrillation," JACC Journals, Dec. 1998, vol. 32 Issue 7, p. 2065-2071.

Darrell Etherington, Ring's newest security camera is a $249 autonomous indoor drone shipping in 2021, TechCrunch.com, Sep. 24, 2020. https://techcrunch.com/2020/09/24/rings-newest-security-camera-is-a-249-autonomous-indoor-drone-shippig-in-2021/.

Zoll, LifeVest, Proven protection from Sudden Cardiac Death, 2017, 4 pages. Pittsburgh PA, USA.

International Search Report and Written Opinion for PCT Application No. PCT/US2015/051726, dated May 20, 2016, European Patent Office, Rijswijk, 11 pages.

* cited by examiner

FIG. 4    *SAMPLE COMPONENTS OF EA DEVICE*

AUTONOMOUS EVENT ASSISTANT DEVICE

CROSS-REFERENCE(S) TO RELATED APPLICATION(S)

This application claims the benefit of U.S. Provisional Application No. 63/069,638 filed Aug. 24, 2020, entitled Autonomous Visual Event Assistant (AVEA), which is expressly incorporated herein by reference in its entirety for all purposes.

BACKGROUND

In some cases, for example, when a cardiac arrest or stroke occurs, if the victim is left unattended, the risk of detrimental outcome, including death, increases rapidly with each passing minute. Individuals at risk of falling and/or losing consciousness due to age or a health condition may benefit from a wearable monitoring device, and in some cases, from a wearable treatment device. Wearable health devices can monitor and record detected health events. Wearable treatment devices can further treat a detected event.

SUMMARY

This summary is provided to introduce a selection of concepts in a simplified form that are further described below. This summary is not intended to identify key features of the claimed subject matter, nor is it intended to be used as an aid in determining the scope of the claimed subject matter.

The present disclosure describes examples of health monitoring systems with an event assistant (EA) device. The EA device, responsive to a monitoring device's detection of the monitored event, can navigate to the monitoring device and obtain information about the wearable monitoring device. The obtained information may include a status of wearer wearing the wearable monitoring device. The obtained information can also be communicated to a rescuer, which may be a caregiver and/or rescue dispatch center or directly to a local emergency response team.

DETAILED DESCRIPTION

The description set forth below in connection with the appended drawings is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

Figure 1:
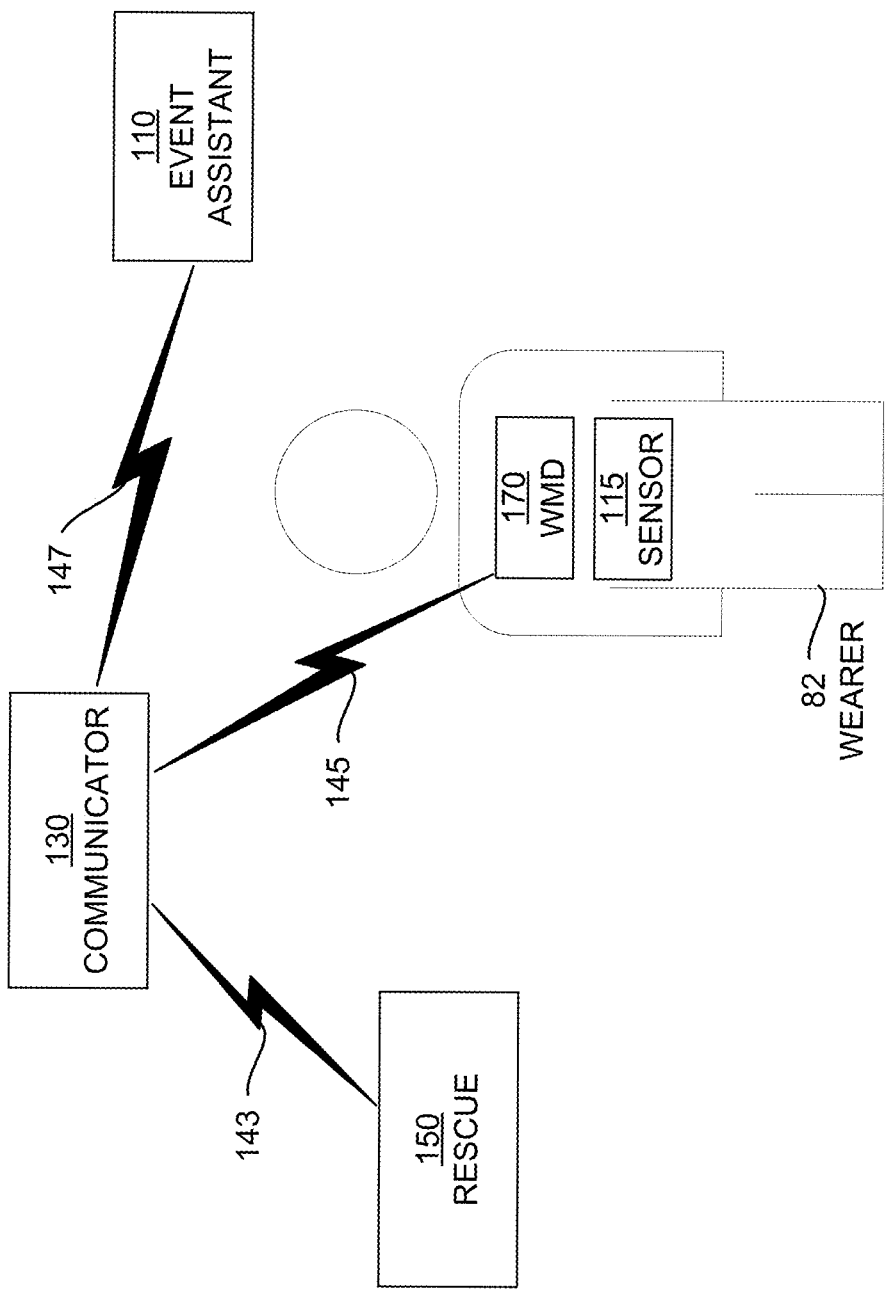
FIG. 1 is a conceptual diagram of a monitoring system with a wearable monitoring device, a communicator, and an event assistant device, according to embodiments.

FIG. 1 depicts a monitoring system, in accordance with embodiments. In one embodiment, a wearer 82 is a person using a wearable monitoring device (WMD) 170. The WMD 170 is configured to sense specific physiological signals of the wearer 82 and recognize when the signals are indicative of an event, such as a medical emergency, for example a cardiac arrest event, an event where the wearer 82 may lose consciousness and which may require a rescue dispatch.

In embodiments, when an event is detected, the WMD 170 can send information about the event to another device, such as a communicator 130. The communicator 130 receives the information and signals an event assistant (EA) device 110. The communicator 130 can provide a location to the EA device 110. The EA device 110, upon receipt of the information about the location of either the WMD 170 or the communicator 130, can navigate towards the provided location by self-driving or flying, or both.

Figure 3:
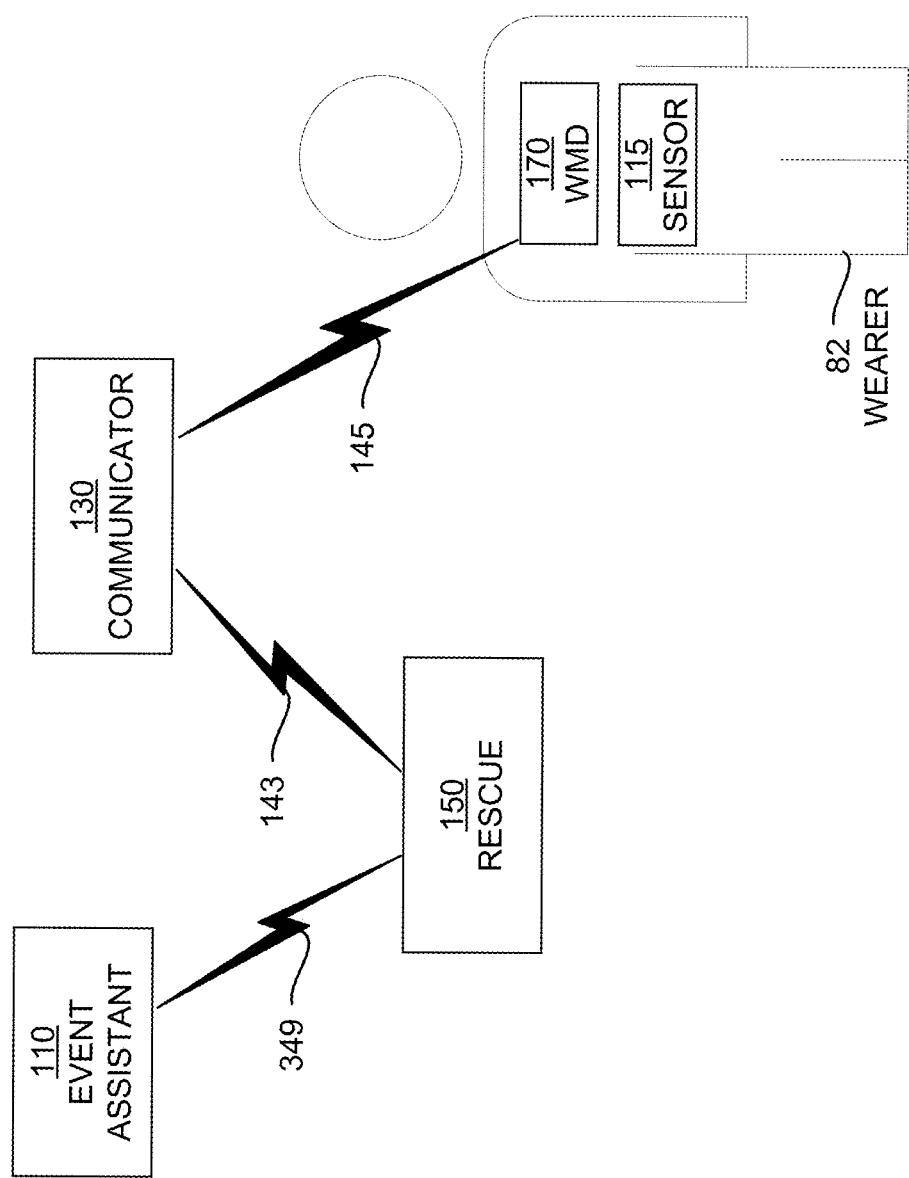
FIG. 3 is a conceptual diagram of a monitoring system with a wearable monitoring device, a communicator, and an event assistant device, according to embodiments.

The EA device 110 upon finding the location can obtain visual, video, photo, and/or audio information of the area where the WMD 170 is located. The video, photo, and/or audio captured of the area can be provided to the rescue 150 via the communicator 130. In some embodiments, the captured information can be communicated directly to a rescuer, as illustrated in FIG. 3.

By capturing information during the "blind" time, the EA device 110 may facilitate more expedient rescue and care. A professional rescue dispatch or a designated caregiver may be able to assess the situation using the captured information and form an understanding of the urgency, needed resources, and may be able to optimize any care handoff time and approach.

Embodiments of a WMD 170 include an external ambulatory device, and can include any one or a combination of the following devices: a wearable cardioverter defibrillator (WCD), an ECG monitor, a heart rate monitor, a heart pacing device, a blood pressure monitor, a hemodynamic monitor, a heart sound monitor, an AF burden monitor, a sleep apnea monitor, a posture monitor, a glucose monitor, any device configured to continually monitor for a health condition or status. In other embodiments, instead of WMD 170, implantable or subcutaneous devices can be used to continually monitor the patient for a health condition or status.

In embodiments, the WMD 170 may be configured to communicate information to the communicator 130 via a wired or wireless communication link 145. The communication link 145 may be a short-range communication link, including but not limited to, a Bluetooth, Near Field Communication (NFC), infrared, ultra-wide band, wireless regional area networks, low power wireless P2P, Wireless HART, Wireless HD, USB, RFID, ZigBee, Z-Wave, etc. Other types of communication links are possible. In some embodiments, the communicator 130 and the WMD 170 can be integrated and/or include a wired communication link.

In some embodiments, the communication link 143 between the communicator 130 and rescue 150 can be a wireless data link, including but not limited to, LTE, 4G, 5G, cellular link (e.g., voice or SMS). The wireless link 147 between the communicator 130 and the event assistant device 110 can be a Bluetooth, a Wi-Fi, NFC, infrared, ultra-wide band, wireless regional area networks, low power wireless P2P, Wireless HART, Wireless HD, USB, RFID, ZigBee, Z-Wave, etc. Other types of communication links are possible.

In some embodiments, the communicator 130 can be a WLAN access point, a Wi-Fi, cellular, 4G, 5G. In some embodiments, the communicator 130 can be a base station, such as a cell tower, configured as a transceiver that can send and receive signals and connect the EA device 110, and/or the WMD 170 to other networks or devices, such as an EMT network or device, or 911 dispatch, or a WMD private centralized care network, etc.

In other embodiments, the communicator 130 can be configured as a home device hub connecting devices such as WMD 170, EA device 110, and/or other personal and/or home devices such as wearable sensor 115, and integrating health monitoring of the wearer 82. In one embodiment, the communicator 130 is a smart controller that can include features of a smart phone or other gadgets configured to control lights, thermostats, home cameras, door emergency access, etc. In one embodiment, when the wearer 82 suffers a cardiac event, the communicator 130 can receive information from a door camera, for example and determine if a person at the door is a rescuer and unlock the door using the security settings in place in case of the cardiac arrest event.

Embodiments of a communicator 130 further include, but are not limited to, a tablet, a laptop computer, a smartwatch, a cell phone. The communicator 130 can be configured to communicate detection of an event to the EA device 130 and a location or an approximate location of the WMD 170. The approximate location to the WMD 170 can be based the location of the communicator 130 or another GPS beacon device, such as the sensor 115.

In embodiments, the communicator 130, in response to receiving an event information from the WMD 170, transmits a signal to the EA device 110 along with its location. Alternatively, the communicator 130, upon receiving information from the WMD 170 about the event, can also receive the location coordinates information from the WMD 170, which can then be used to navigate the EA device 110 to the WMD 170. In yet another embodiment, upon receiving information from the WMD 170 about an event, the communicator 130 can be configured to receive location coordinates information from another device on the wearer, such as a sensor 115 and use the sensor location information to navigate the event assistant 110 to the wearer 82.

Embodiments of the EA device 110 include, but are not limited to, a gadget device, which is has a flight and/or driving and/or surveillance capability, examples which include a drone, a bot, a minidrone, a microdrone, a nanobot, or a robot.

The EA device 110 can be configured to navigate to another device, such as the communicator 130 or the WMD 170 or another sensor 115. The EA device can be configured to receive information that triggers it to navigate to a location where the EA 110 device can obtain at least one of a visual and/or audio information of the location it is dispatched to. The EA device can be configured to fly and hover over the location while its camera, and/or speaker, and/or video capture is turned on. The captured surveillance data, visual and/or audio, can be transmitted to the communicator 130 via the communication link 147. Alternatively, the scene video/picture/audio can be streamed directly to rescue 150 and/or be simultaneously recorded for the rescuers before their arrival at the scene.

The EA device 110 can be configured to detect movement of a nonwearer and terminate obtaining information upon detection of a bystander movement. The EA device 110 can further be configured to detect a bystander speech and similarly terminate obtaining information when bystander speech is detected. In another embodiment, when a bystander is detected, the EA device can act as a coach for what to do. If it does not detect a bystander within a certain perimeter, it could sound a loud alert to summon help. In one scenario, the EA device 110 stays near a WMD 170 and harvests observation information for the rescuers. In another case, the EA device 110 may scope increasingly larger perimeter to detect human bystanders and summon them to rescue. In another embodiment, the EA device 110 can be configured to determine that a professional rescuer, such as EMT are present and communicate handoff information Embodiments of rescue 150 include, but are not limited to a dispatch center, Public Safety Answering Point (PSAP), emergency medical response team network and/or device, a designated caregiver device and/or network, for example a family member, a nurse, a physician, a wearable medical system service staff, etc. Embodiments of rescue 150 can also include vehicle emergency systems.

The wearer 82 may be considered a patient. The wearer 82 can also be considered a "user" of the monitoring system, but this is not a requirement. For instance, a user may also be rescue 150, and may include a clinician such as a doctor, nurse, emergency medical technician (EMT), rescue dispatch center staff, a designated caregiver, or other similarly tasked individual or group of individuals. The context of these and other related terms within this description should be interpreted accordingly.

A wearer's life signal can include, but are not limited to, the wearer's body motion, voice, eye movement, or a physiological signal. Physiological signals can include, but are not limited to, an electrocardiogram signal, heartbeat, heart rate, impedance, conductivity, glucose levels. Physiological signals can include wearer's 82 nerve twitching, shaking, skin color, lack of muscle movement information, perspiration, oxygen saturation, apnea. Physiological signals can also include vital sign signals such as wearer's temperature, pulse rate, respiration rate, blood pressure.

The monitoring system of FIG. 1, according to embodiments, can obtain data from the wearer 82. For collecting additional data, the system may optionally include at least an outside sensor 115. The sensor 115 could be provided as a standalone device, for example not coupled in any way to the WMD 170. The sensor 115 may sense or monitor at least one additional wearer signal. The wearer 82 may wear the sensor 115, to, for example, supplement the event information provided by the WMD 170. For example, the sensor 115 may provide temperature, or respiration rate or the wearer 82, body movement, muscle movement, glucose levels, and so on. The sensor 115 could alternatively provide environmental information of the wearer 82, such as ambient temperature, altitude, carbon monoxide detection, humidity, motion detection, etc. The sensor 115 can be configured to aid the EA device in providing location coordinates and/or in maintaining a range and/or angle of view within the WMD 170 and/or the wearer 82. Sensor 115 can be a proximity sensor aiding the EA device 110 in finding the location and distance from the WMD that can optimize video, photo, audio acquisition.

Figure 2:
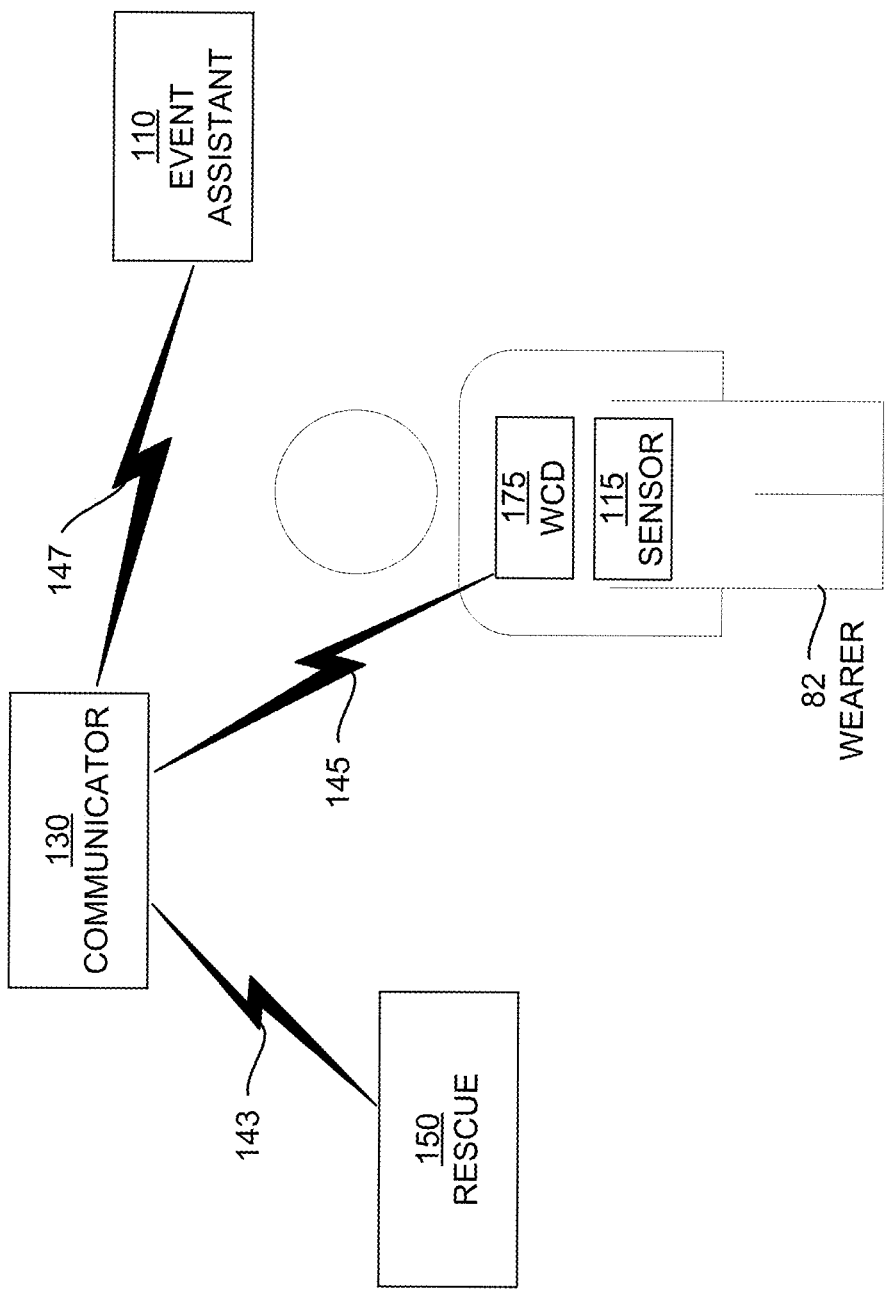
FIG. 2 is a conceptual diagram of a monitoring system with a wearable cardioverter defibrillator device, a communicator, and an event assistant device, according to embodiments.

FIG. 2 illustrates an embodiment similar to the embodiment of FIG. 1, but where the monitoring system includes a wearable monitoring device, which further includes a wearable treatment device. In an embodiment, the wearable treatment device can be a wearable cardioverter defibrillator (WCD) 175. As described in, for example, the U.S. Pat. No. 9,539,437, titled: "Wearable Cardiac Defibrillator System Sensing Being Touched by Bystander," or the U.S. Pat. No. 8,838,235, titled: "Wearable Defibrillator System Communicating via Mobile Communication Device," both incorporated herein by reference for all purposes, WCD 175 can include a support structure such as a garment or a vest, a belt or a band, an electronics module, which can be attached to the support structure. The electronics module obtains physiological sensor of the wearer 82. The WCD 175 also comprises a processor which communicates with the electronics module, and processes information based on the sensed physiological signal information to determine if an event is occurring and/or therapy is applied. In embodiments described here, WCD 175 communicates the event information to the communicator 130 and the communicator 130 communicates the event information to rescue 150 and to the event assistant 110.

FIG. 3 illustrates an embodiment where the EA device 110 transmits the obtained event information, whether audio or visual or both, directly to the rescue 150, bypassing the communicator 130. The communicator 130 can communicate the event information received from the WMD 170 directly to the rescue independently of the EA device 110. In further embodiments, WMD 170 or sensor 115 may signal the EA device 110 with their location information and summon the EA device 110 to that location, bypassing the communicator 130. In still further embodiments, the EA device 110 comprises at least one or more of the modules of the communicator 130.

In embodiments, the WMD 170 communicates information to the communicator 130 via a wired or wireless communication link 145. The communication link 145 can be a short range communication link, including but not limited to, a Bluetooth, Near Field Communication (NFC), infrared, ultra-wide band, wireless regional area networks, low power wireless P2P, Wireless HART, Wireless HD, USB, RFID, ZigBee, Z-Wave, etc. Other types of communication links are possible. In some embodiments, the communication link 143 between the communicator 130 and rescue 150 can be a wireless data link, including but not limited to, LTE, 4G, 5G, cellular link (e.g., voice or SMS), Bluetooth, a Wi-Fi, NFC, infrared, ultra-wide band, wireless regional area networks, low power wireless P2P, Wireless HART, Wireless HD, USB, RFID, ZigBee, Z-Wave, etc. Similarly, the communication link 349 between the event assistant device 110 and a rescue 150 device can be, including but not limited to, LTE, 4G, 5G, cellular link (e.g., voice or SMS), Bluetooth, a Wi-Fi, NFC, infrared, ultra-wide band, wireless regional area networks, low power wireless P2P, Wireless HART, Wireless HD, USB, RFID, ZigBee, Z-Wave, etc. Other types of communication links are possible.

In some embodiments, a person living with an increased risk of a potentially life threatening condition that could at any moment incapacitate him/her, cause a fall and/or loss of consciousness, may find it stressful to be alone for any length of time, even if wearing a monitoring system and/or treatment device. Individuals in such situations may find comfort that such a monitoring system, and/or treatment system includes an EA device 110, and that the EA device 110 can obtain information about their status when a life threatening event occurs and nobody may be present to witness the event. Wearers of such monitoring systems, and treatment systems, such as a wearable cardioverter defibrillator, may find it reassuring that should they become unconscious, the EA device 110 can obtain information during the "blind" time, which is the time between the event onset and when the rescue arrives, the time during which the wearer may not be conscious, or even if conscious, may not remember, and when no bystanders may be present. Information obtained during this time can be helpful in expediting care and/or patient information handoff to a rescuer.

Figure 4:
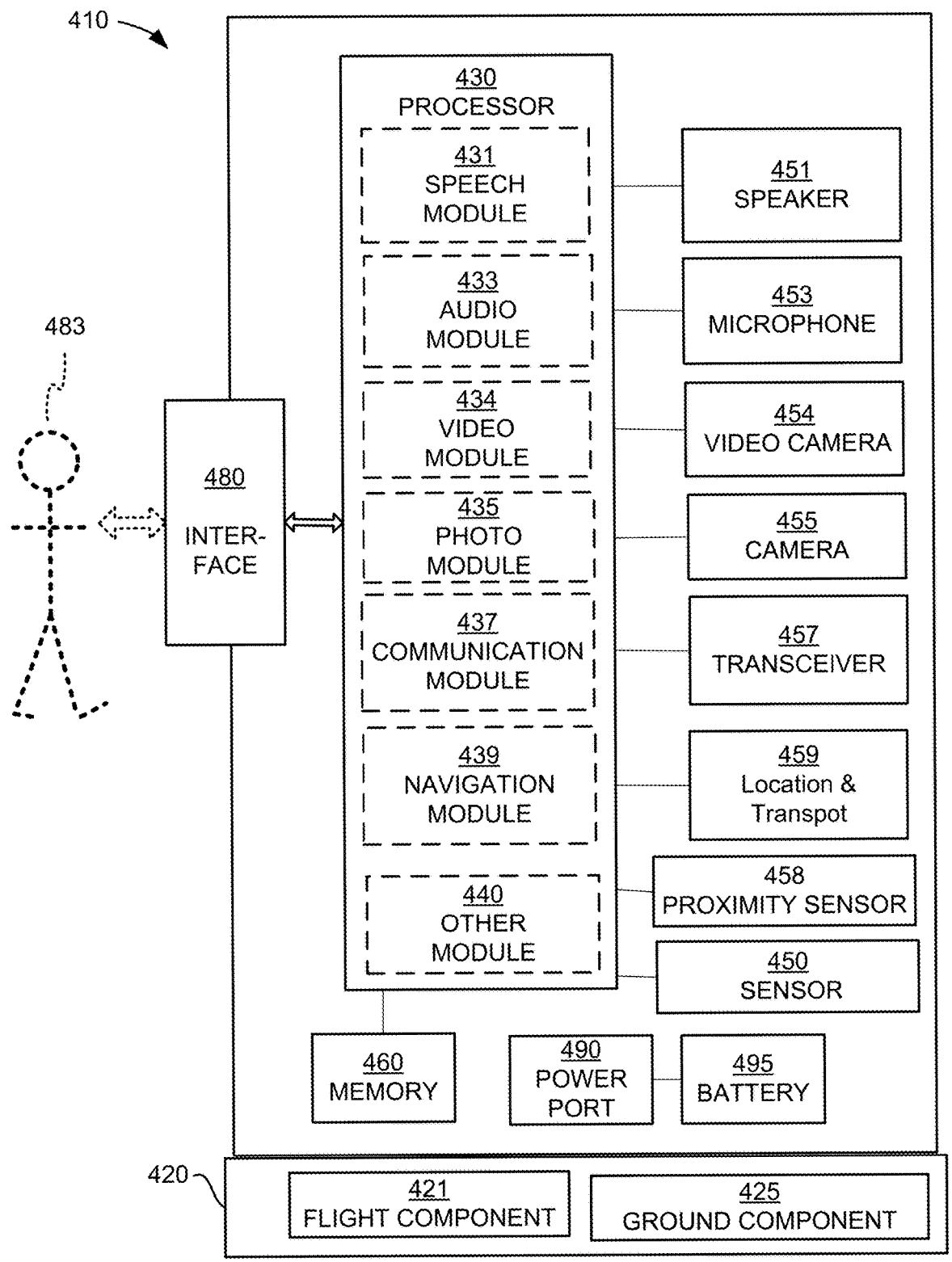
FIG. 4 is a block diagram illustrating sample components of an event assistant device, according to embodiments.

FIG. 4 is a diagram showing sample components of an EA device 410, which in some embodiments is similar to the EA device as shown in FIGS. 1-3. A processor 430 of the EA device 410 can further include various processing modules, including but not limited to, a speech module 431, which can be configured to process speaker 451 content, including any sounds containing alerts, warnings, metronome, instructions, such as CPR instructions to bystanders; audio module 433 configured to process information obtained by the microphone 453. The processor's 430 speech module 431 in tandem with the audio module 433 can further comprise a natural speech recognition and utilize the speaker 451 and the microphone 453 to interact with a user 483 who may be a bystander, a rescuer, or the wearer of the WMD via the interface 480.

The processor 430 may also include a video module 434 configured to process information obtained by the video camera 454, the photo module 435 configured to process information obtained by the still photo camera 455. In some embodiments a single camera may be used to implement both video camera 454 and still photo camera 455. The interface 480 can further enable the user 483 to access the obtained photo, sound, and/or video information.

The processor's 430 communication module 437 can receive information about an event, for example information that the event is a cardiac arrest event, time of detection, and a location information for the WMD 170, shown in FIGS. 1 and 3, or the WCD 175, shown in FIG. 2, and communicate this information along with any new visual and/or audio captured information to the communicator 130, as shown in FIGS. 1 and 2, and/or a user 483, and/or a user 483 who is rescue 150 rescue 150, as shown in FIG. 3.

In one embodiment, the EA device 410 can stream in real or close to real time what it sees to a remote rescue either directly or via an intermediary, such as the communicator 130.

In another scenario, the EA device detects and can coach a bystander on what is happening and/or what needs to be done, for example, the EA device can coach a bystander to apply a cardiopulmonary resuscitation (CPR).

The EA device 410 can further include a sensor 450, which can be a light sensor and which can include an ambient light sensor and help the camera 455 and/or the video camera 454 adjust the vision and use a flashlight feature, if needed. The EA device's sensor 450 can be one or more types of sensors, including a visual sensor, an audio sensor, an infrared sensor, a temperature sensor, ultrawide band sensor, and ambient light sensor.

The EA device 410 further includes a memory 460. The memory 460 can be implemented in a number of ways and may include, but not be limited to, primary memory, RAM, ROM, secondary memory, flash memory. The memory 460 can be accessed by the processor 430 of operation, navigation, communication instructions, including any updates.

The memory 460 can also record and store obtained event information for later retrieval.

The EA device 410 also includes a power port 490 for charging the battery 495. When not navigating or being used in any other way, the EA device 410 can be placed in a charging state, which can be a lower powered or idle state, allowing it receive location information and switch to an operational, navigation and data capture, a higher power consumption state.

Embodiments of the EA device 410 can comprise a transport unit 420. The transport unit 420 can be integrated into the EA device 410. Alternatively, the EA device 410 and the transport unit 420 can be modular and removably coupled, allowing the EA device 410 to be used in various transport configurations. In embodiments, the transport unit 420 enables the EA device 410 to navigate to a location coordinates that the transceiver 457 receives and that the communication module 437 and/or navigation module 439 process. The navigation module 439 can alternatively use a location and transport module 459 input comprising information about its own location vis-à-vis a location received via the transceiver 457 and further engage the navigation unit 420

In some embodiments, the transport unit 420 includes a flight component 421, while in other embodiments the transport unit 420 include a ground component 425, while in still other embodiments the transport unit 420 includes both flight component 421 and ground component 425. The processor 430 comprises a navigation module 439 which receives location information about the WMD 170 and/or the communicator 130. Processor 430 processes this information to determine navigation path and mode, determine whether flying, self-driving and/or hovering is/are required to reach the location, and controls the flight component 421 and/or the ground component 425 of the transport unit 420. The processor 430 can also include other module 440, for other functions, such as for example, CPR assist and instructions for bystanders.

The flight component 421 enables flight navigation and can include, but is not limited to, one or more of the following components: a motor, a propeller, one or more propeller blades, electronics, batteries, GPS module, obstacle avoidance sensor, flight controller.

The ground component 425 enables ground navigation and can include, but is not limited to, one or more of the following components: a motor, electronics, batteries, GPS module, obstacle avoidance sensor, wheels and/or rollers, charging port.

In some embodiments, some components can be utilized by both the flight component 421 and the ground component 425 units.

In embodiments using flight component 421, the EA device 410 can hover and maintain a distance to the wearer, bystanders, rescuers while gathering information. In some embodiments, the EA device can include a proximity sensor 458 which provides information to avoid obstacles while navigating to the location whether during a flight or ground driving. The proximity sensor 458 can further be configured to help the EA device accuracy in finding the location and focusing on the WMD area. The proximity sensor 458 can also include body heat detector or infrared imaging sensor to determine and maintain a distance, such as for example more than one foot distance from the wearer of the WMD and/or a bystander or an obstacle, but that the distance still allows the camera 455 and/or the video camera 454, and/or the microphone 453 capture the location, including the wearer 82 of the WMD.

Figure 5:
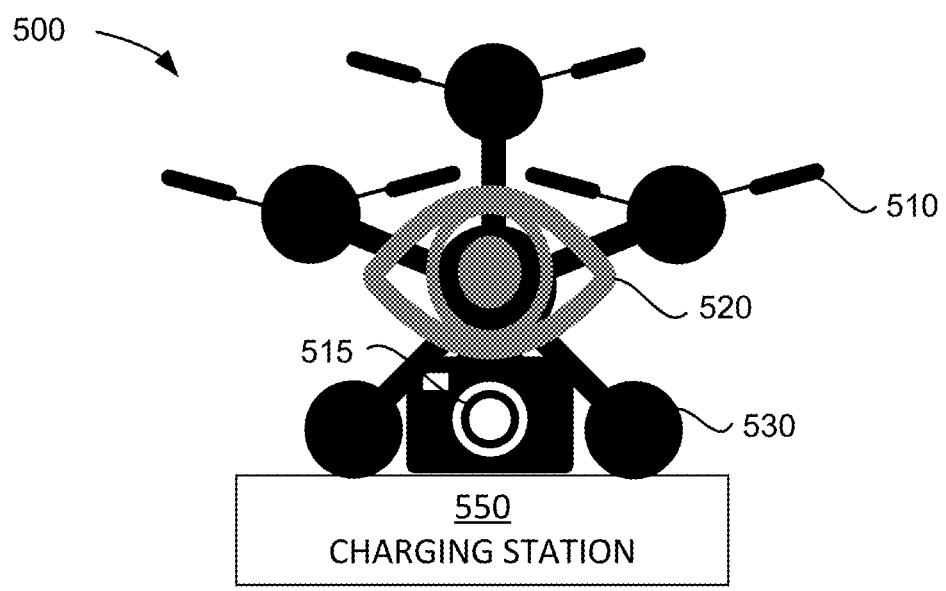
FIG. 5 is a conceptual diagram showing an embodiment of an event assistant device, according to embodiments.

FIG. 5 illustrates an embodiment of an event assistant (EA) device 500 while removably placed in a charging, or resting, state. In FIG. 5, the EA device embodiment 500 includes various components which may include components mentioned with regard to FIG. 4. As mentioned, the EA device 500 can be an autonomous vehicle that, upon receiving a location coordinates, can autonomously navigate toward the received location coordinates, and when within a range of the coordinates, can capture video, photo, and/or audio while maintaining a distance and an angle from the epicenter of the event that is the WMD 170, as shown in FIGS. 1 and 3 or the WCD 175, as shown in FIG. 2. Alternatively, or in addition, in some circumstances, the EA device 500 can be switched to a manual maneuvering by a designated caregiver or rescuer.

The EA device 500 can be, but is not limited to, a gadget such as a bot, a minidrone, a drone, a microdrone capable of autonomous navigation. The EA device 500 can be a combination of an autonomous self-driving vehicle and a drone. The EA device 500 can further be configured to allow for a remote manual navigation by for example a designated caregiver or a rescuer.

Here, for purposes of illustration, the EA device 500 includes one or more propeller blade 510, wheels 530 for ground navigation, camera 515, which can include a speaker, a microphone, an image stabilizer and can take photos or videos. A sensor 520 can be a proximity sensor aiding in navigation and keeping the right distance wearer wearing a WMD. In its monitoring for receiving a location information stage, the EA device 500 can rest on a charging station 550 and/or after the EA device is done capturing visual and/or audio information, the EA device can be further configured to autonomously find its way back and return to the charging station 550.

Figure 6:
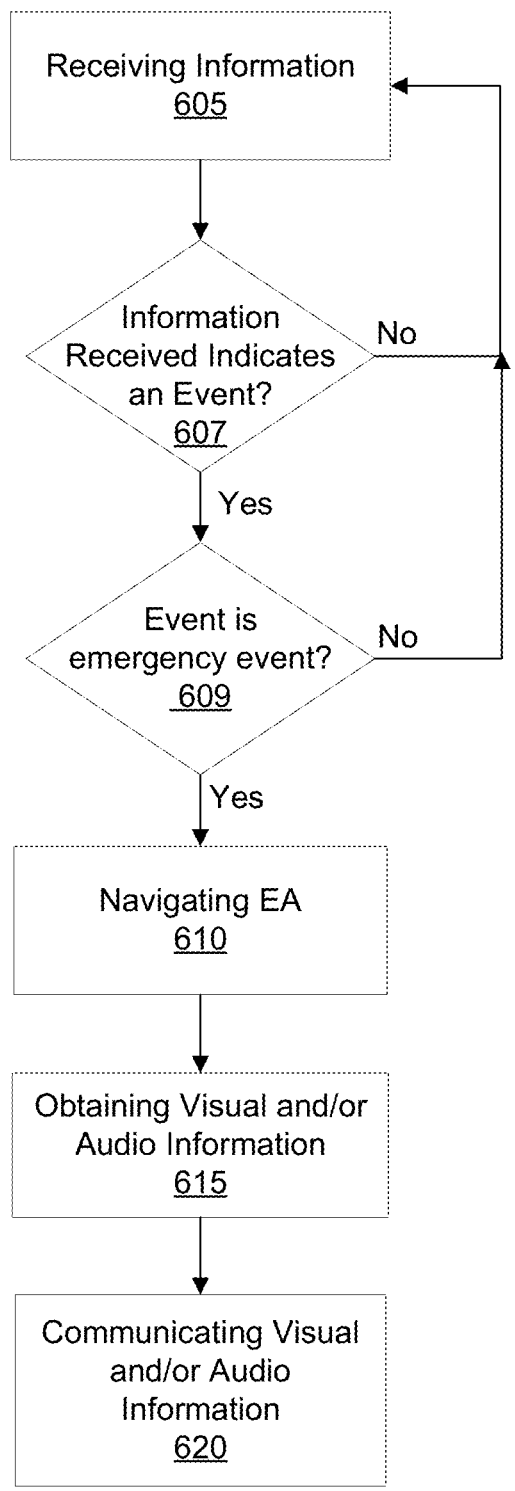
FIG. 6 is a flow chart illustrating steps for obtaining visual and/or audio information based on a determination that an event is an emergency event and based on received location of the event, according to embodiments.

FIG. 6 illustrates a flow chart of a method of communicating information from a wearable monitoring device to a remote location. In one embodiment, at step 605, information is received. For example, in some embodiments a communicator such as the communicator 130 device shown in FIGS. 1-3 receives information from a wearable monitoring device such as the WMD 170 (FIGS. 1, 3) or the WCD 175 (FIG. 2). In other embodiments, a communicator, such as communicator 130 (FIGS. 1-3) can be integrated with an EA device, such as the EA device 110 (FIGS. 1-3), EA device 410 (FIG. 4), EA device 500 (FIG. 5), where the integrated communicator/EA device (not shown) can receive information from a wearable medical device such as the WMD 170 (FIGS. 1, 3) or the WCD 175 (FIG. 2).

At a step 607, a determination is made whether the information received indicates an event a wearer of the wearable monitoring device is being monitored for. In some embodiments, step 607 can be performed by an EA device such as EA device 110 shown in FIGS. 1-3. In other embodiments, step 607 can be performed by a communicator such as communicator 130 shown in FIG. 1-3. If the information does not indicate an event, the process goes back to step 605. If in step 607 it is determined that the received information indicates an event, the process proceeds to a step 609.

In step 609, it is determined whether the event is an emergency event. In some embodiments, step 609 can be performed by an EA device as shown in FIGS. 1-3. In other embodiments, step 609 can be performed by a communicator such as communicator 130 shown in FIG. 1-3. If the event is determined at step 609 to indicate an emergency event information, the process proceeds to a step 610.

In step 610, an EA device is navigated toward an emergency event. In some embodiments, this EA device (e.g., as shown in FIGS. 1-3) performs step 610 autonomously. In some embodiments, information about the emergency event comprising a location information about the event is sent to the EA device. For example, the location information includes coordinates to the EA device which the EA device uses to navigate it to the approximate location of the WMD device. In another embodiment, step 610 can be performed remotely by a rescuer, such as rescue 150 as shown in FIGS. 1-3.

In a step 615, visual and/or audio information is obtained by the EA device. In some embodiments, following step 610 the EA device, such as the EA device 110, 410, 500 shown in FIGS. 1-3, 4, and 5 respectively, upon arriving at a location, obtains visual and/or audio information. In some embodiments, the location is a point within a predefined range of the location information received as described in step 610. In other embodiments, the location is determined by the EA device by sensing a beacon signal provided by a WMD, such as the WMD 170 (FIGS. 1, 3), or a WCD such as a WCD 175 (FIG. 2), or a sensor, such as sensor 115 (FIGS. 1-3). In another embodiment, the location is determined by the EA device sensing a beacon provided by a communicator, such as the communicator 130 (FIGS. 1-3).

In a step 620, the information obtained in step 615 is communicated to a remote location. In some embodiments, step 620 is performed by an EA device to communicate the obtained information to the remote location. For example, an EA device such as EA device 110 as shown in FIGS. 1-3. In some embodiments, EA device 410 (FIG. 4), or EA device 500 (FIG. 5) can communicate the obtained information to a rescue such as rescue 150 (FIGS. 1-3) via a communicator such as communicator 130 (FIGS. 1-3). In some embodiments, an EA device such as the EA device 110 of FIGS. 1-5, can be configured to obtain visual and/or audio information of the area where the WMD and/or the communicator are located and provide visual and/or audio information to the communicator, which can then be communicated by the communicator to a rescuer.

Figure 7:
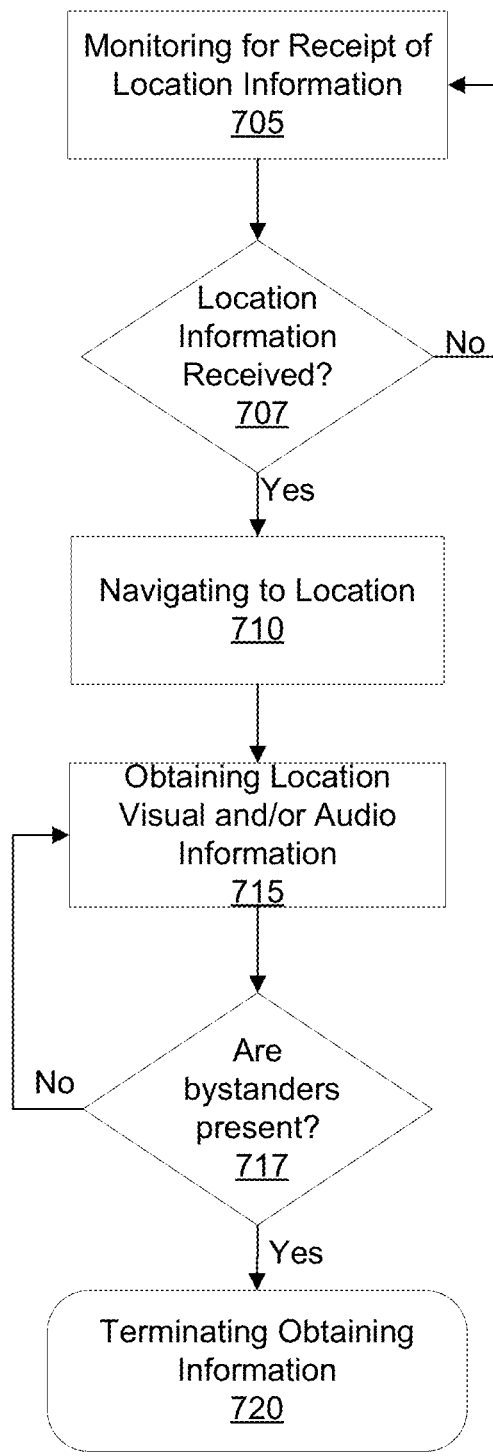
FIG. 7 is a flow chart illustrating navigation of the EA device to a location and obtaining of location information, according to embodiments.

FIG. 7 illustrates a flow chart of a method of communication information from a wearable monitoring device to a remote location. In one embodiment, at step 705, location information is received. For example, in some embodiments a communicator such as the communicator 130 device shown in FIGS. 1-3 receives information from a wearable monitoring device such as the WMD 170 (FIGS. 1, 3) or the WCD 175 (FIG. 2). In some embodiments, an EA device, such as the EA device 110 (FIGS. 1-3), EA device 410 (FIG. 4), or EA device 500 (FIG. 5) is configured to receive information from a wearable medical device such as the WMD 170 (FIGS. 1, 3) or the WCD 175 (FIG. 2) either directly or via the communicator 130. In other embodiments, a communicator, such as communicator 130 (FIGS. 1-3) can be integrated with an EA device, such as the EA device 110 (FIGS. 1-3), EA device 410 (FIG. 4), or EA device 500 (FIG. 5), and the integrated communicator/EA device can receive information from a wearable medical device such as the WMD 170 (FIGS. 1, 3) or the WCD 175 (FIG. 2).

Step 705 is a step of vigilance and monitoring for receipt of a location information. For example, the EA device, such as the EA device 110 (FIGS. 1-3), EA device 410 (FIG. 4), EA device 500 (FIG. 5), monitors for a receipt of a location information from a wearable device, such as the WMD 170 (FIGS. 1, 3) or WCD 175 (FIG. 2), and/or from the communicator 130 (FIGS. 1-3).

At a step 707, a determination is made whether location information is received. If location information is not received, the process returns to step 705. In some embodiments, step 707 can be performed by an EA device such as EA device 110 shown in FIGS. 1-3, EA device 410 shown in FIG. 4, or EA device 500 shown in FIG. 5. If, in step 707, it is determined the received information includes location information, the process proceeds to step 710.

In step 710, an EA device navigates toward the location received. In some embodiments, the location information is used to includes coordinates to the EA device which the EA device uses to navigate it to that or an approximate location of a WMD device, such as WMD 170 as shown in FIGS. 1 and 3.

In step 715, visual and/or audio information is obtained. In some embodiments, following step 710, the EA device, upon arriving at a location, obtains visual and/or audio information. In some embodiments, step 715 is performed by an EA device, such as EA device 110, 410, 500 shown in FIGS. 1-3, 4, 5, respectively. In some embodiments, the location is a point within a predefined range of the location information received as described in step 710.

In other embodiments, the location is determined by the EA device sensing a beacon signal provided by a wearable device, such as the WMD 170 (FIGS. 1, 3), or a WCD such as a WCD 175 (FIG. 2), or a sensor, such as sensor 115 (FIGS. 1-3). In other embodiments, the location is determined by the EA device by sensing a beacon provided by a communicator, such as the communicator 130 (FIGS. 1-3).

In a step 717, bystander presence is determined, based on, for example, a voice and/or motion detection, a non-wearer body heat detection. In some embodiments, step 717 is performed by an EA device as shown in FIGS. 1-5. If no bystanders are detected, step 715 is performed and visual and/or audio information is obtained. If bystanders are detected, obtaining of visual and/or audio information is terminated at step 720.

In a step 720, the information obtained in step 715 can be communicated to a remote location. In some embodiments, step 720 is performed by an EA device to communicate the obtained information to the remote location. For example, an EA device such as the EA device 110 (FIGS. 1-3), 410 (FIG. 4), 500 (FIG. 5) can communicate the obtained information to a rescue such as rescue 150 (FIGS. 1-3) and/or a user 483 (FIG. 4), via a communicator such as a communicator 130 (FIGS. 1-3). In some embodiments, an EA device, such as the EA device 110 (FIGS. 1-3), can be configured to obtain visual and/or audio information of the area where the WMD and/or the communicator are located and provide visual and/or audio information to the communicator, which can then be communicated by the communicator to a rescuer. In some embodiments, an EA device can store the obtained visual and/or audio information for later retrieval by a user, such as a user 483 shown in FIG. 4.

Figure 8:
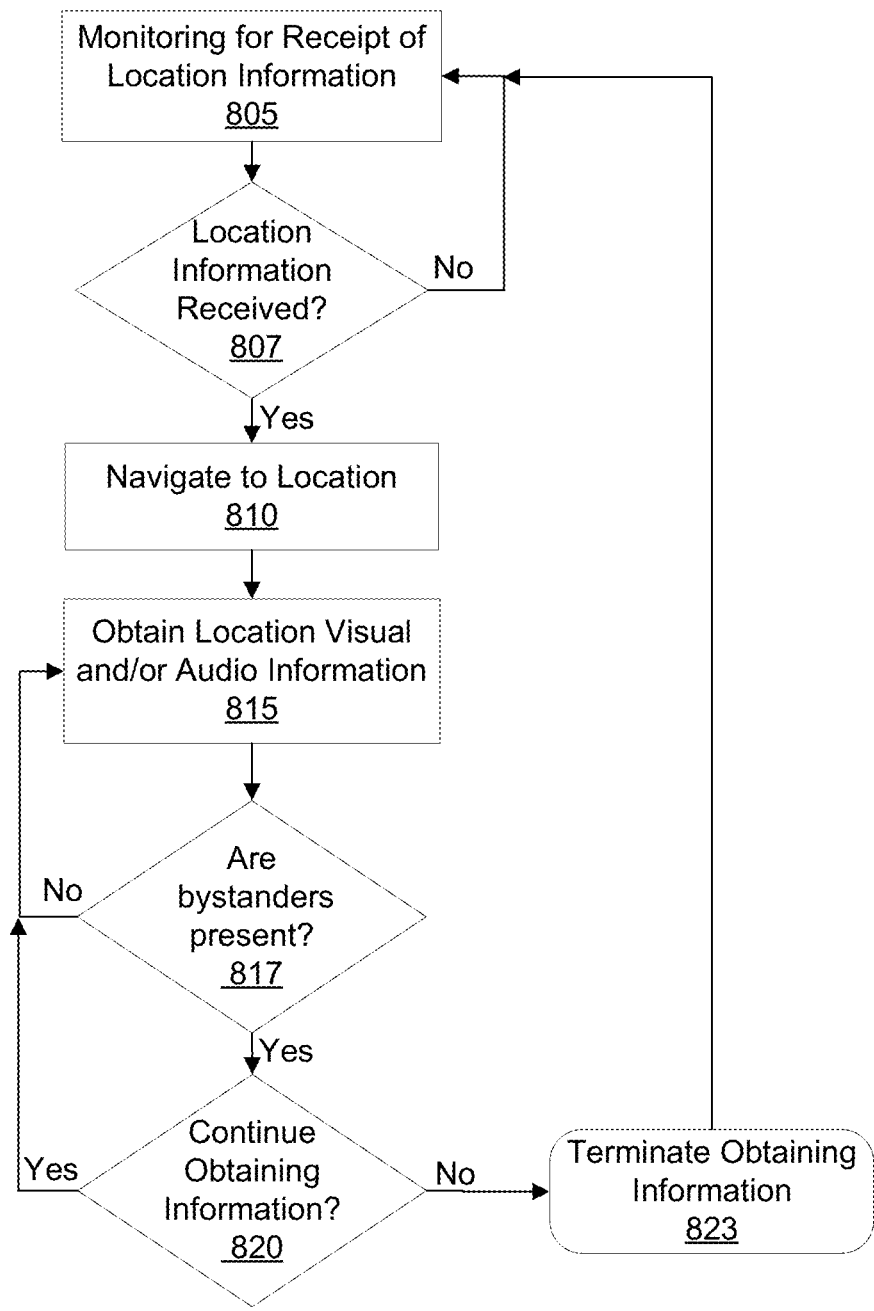
FIG. 8 is flow chart illustrating navigation of the EA device to a location and obtaining of location information, according to embodiments.

FIG. 8 illustrates a flow chart of a method for receiving information. At 805, the method monitors for a receipt of location information. Similarly, to FIGS. 6 and 7, step 805 can be performed by the EA device, which monitors for receiving a location information. At step 807, determining if the location information is received. If not received, the method returns to step 805. If, at step 807, it is determined the received information includes location information, the process proceeds to a step 810.

At step 810, an EA device navigates toward the location received. In some embodiments, the location information used includes coordinates which the EA device uses to navigate to an approximate location of a WMD device, such as WMD 170 as shown in FIGS. 1 and 3.

When at the location, at step 815, the method obtains visual and/or audio information. In some embodiments, at step 817, the method senses when bystanders are present. At step 820, the method may determine whether to continue obtaining information by interacting with the bystander and asking whether to continue obtaining information if or terminate obtaining information. In some embodiments, at step 823, the method may terminate obtaining information. If the method continues to obtain information, then at step 815, the method may obtain visual and/or audio information of the location. If obtaining information is terminated, the method returns to step 805.

In one example, when a user 483 (FIG. 4) turns the EA device off or instructs the EA device to terminate obtaining visual and/or audio of a scene, the EA device terminates obtaining further information. In a further embodiment, the method may return to step 805. In yet a further embodiment, the EA device can terminate obtaining of the information at the location. In yet another embodiment, the EA device may self-navigate to a charging station and resume monitoring for next receipt of location information.

Other embodiments include combinations and sub-combinations of features described or shown in the drawings herein, including for example, embodiments that are equivalent to: providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, feature or features can refer to the structures and/or functions of an apparatus, article of manufacture or system, and/or the steps, acts, or modalities of a method.

What is claimed is:

1. A monitoring system, comprising:
    a wearable monitoring device configured to sense physiological signals of a wearer to detect an event triggered by the wearer experiencing a medical condition;
    a communicator configured to receive information indicative of the event from the wearable monitoring device and to transmit a communication in response to the detection of the event; and
    an event assistant (EA) device configured to, responsive at least in part to the communication:
        navigate to a location of the wearable monitoring device,
        upon reaching the location, detect a human bystander within a certain perimeter of the wearer, wherein the human bystander is detected by scoping increasingly larger perimeter from the wearer, and
        provide instructions for the human bystander on how to treat the medical condition.

2. The monitoring system of claim 1, wherein the wearable monitoring device comprises a cardiac monitoring device, the cardiac monitoring device comprising:
    a support structure configured to be worn by the wearer and to position one or more sensors to sense the physiological signals of the wearer;
    an electronics module; and
    a processor disposed in the electronics module and configured to, based on the sensed physiological signals of the wearer, detect the event and trigger rescue dispatch.

3. The monitoring system of claim 1, further comprising a therapy device communicatively coupled to the wearable monitoring device, the therapy device configured to administer a therapy based on the sensed physiological signals, wherein the EA device is further configured to issue an alert for the human bystander that the therapy device is administering the therapy.

4. The monitoring system of claim 3, wherein the therapy device comprises a wearable cardioverter defibrillator.

5. The monitoring system of claim 1, wherein the communicator is further configured to:
    alert a rescue dispatch center;
    receive information obtained by the EA device; and
    transmit, to the rescue dispatch center, the information obtained from the EA device.

6. The monitoring system of claim 1, wherein the EA device comprises a minidrone.

7. The monitoring system of claim 1, wherein the EA device comprises a bot.

8. The monitoring system of claim 1, wherein the EA device is further configured to obtain at least one of visual information or audio information about the wearable monitoring device.

9. The monitoring system of claim 1, wherein the EA device is further configured to:
    obtain information about the wearable monitoring device; and
    transmit the obtained information to the communicator.

10. The monitoring system of claim 1, wherein the EA device includes an ultra-wide bandwidth sensor.

11. The monitoring system of claim 1, wherein the EA device includes one or more audio sensors.

12. The monitoring system of claim 1, wherein the communication of the detection of the event comprises at least one of: a location of the communicator or a location of the wearable monitoring device.

13. The monitoring system of claim 1, wherein the EA device is configured to navigate by performing at least one of the following actions: flying, autonomous driving, or hovering.

14. The monitoring system of claim 13, wherein the at least one action comprises at least one action occurring within a range of the wearable monitoring device.

15. The monitoring system of claim 1, wherein when the EA device does not detect the human bystander within the certain perimeter of the wearer, the EA device is further configured to transmit an audio alert for medical assistance.

16. A method of monitoring a health of a patient wearing a wearable medical device (WMD), the method comprising:
    receiving physiological signals of the patient;
    detecting an event triggered by the patient experiencing a medical condition;
    transmitting a communication in response to the detection of the event; and
    responsive at least in part to the communication, causing an event assistant (EA) device to navigate to a location of the WMD, wherein the EA device is configured to:
    upon reaching the location, detect a human bystander within a certain perimeter of the patient, wherein the human bystander is detected by scoping increasingly larger perimeter from the patient, and
    provide instructions for the human bystander on how to treat the medical condition.

17. The method of claim 16, wherein the EA device is further configured to issue an alert for the human bystander that a therapy device is administering therapy, the therapy device being communicatively coupled to the WMD.

18. The method of claim 16, wherein the EA device is further configured to obtain at least one of visual information or audio information about the WMD.

19. The method of claim 18, wherein the EA device is further configured to detect a speech of the human bystander.

20. The method of claim 16, further comprising:
    alerting, by the communicator, a rescue dispatch center;
    receiving, by the communicator, information obtained by the EA device; and
    transmitting, by the communicator, to the rescue dispatch center the information obtained from the EA device.

* * * * *